United States Patent
Zhang et al.

(10) Patent No.: US 11,436,730 B2
(45) Date of Patent: Sep. 6, 2022

(54) TEMPERATURE-SENSITIVE TRIGGER SKEW CORRECTION

(71) Applicant: Siemens Medical Solutions USA, Inc., Malvern, PA (US)

(72) Inventors: Nan Zhang, Knoxville, TN (US); Martin Judenhofer, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 217 days.

(21) Appl. No.: 16/860,312

(22) Filed: Apr. 28, 2020

(65) Prior Publication Data
US 2021/0334973 A1   Oct. 28, 2021

(51) Int. Cl.
G06T 7/00 (2017.01)
A61B 5/055 (2006.01)
A61B 6/03 (2006.01)

(52) U.S. Cl.
CPC ............ G06T 7/0016 (2013.01); A61B 5/055 (2013.01); A61B 6/037 (2013.01); G06T 2207/10104 (2013.01)

(58) Field of Classification Search
CPC ......... G06T 7/0016; G06T 2207/10104; A61B 5/055; A61B 6/037
USPC ....................................................... 382/131
See application file for complete search history.

(56) References Cited

U.S. PATENT DOCUMENTS

| 8,089,037 B2 | 1/2012 | Schmand et al. | |
|---|---|---|---|
| 9,874,587 B1 * | 1/2018 | Holcomb | G01R 13/0254 |
| 2010/0065723 A1 * | 3/2010 | Burbar | G01T 1/1648 |
| | | | 250/214 AG |

FOREIGN PATENT DOCUMENTS

WO   WO-2012137109 A2 *   10/2012   ........... G01T 1/2985

OTHER PUBLICATIONS

McIntre, R. J., "Theory of Microplasma Instability in Silicon", Journal of Applied Physics, vol. 32, No. 6, Jun. 1961, (pp. 983-995, 13 total pages).

Haitz, Roland H., "Model for the Electrical Behavior of a Microplasma", Journal of Applied Physics, vol. 35, No. 5, May 1964, (pp. 1370-1376, 7 total pages).

Cova, S. et al., "Avalanche photodiodes and quenching circuits for single-photon detection", Applied Optics, vol. 35, No. 12, Apr. 20, 1996, (pp. 1956-1976, 21 total pages).

Corsi, F. et al., "Modelling a silicon photomultiplier (SiPM) as a signal source for optimum front-end design", Nuclear Instruments & Methods in Physics Research A 572 (2007), DOI:10.1016/j.nima.2006.10.219, (pp. 416-418, 3 total pages).

(Continued)

*Primary Examiner* — Wednel Cadeau

(57) ABSTRACT

Systems and methods include determination of a first relationship between change in photopeak energy and event time skew based on a first detection event signal acquired from a detector at a first temperature and a subsequent detection event signal acquired from the detector at a next temperature, acquisition of a subsequent detection event signal from the detector, determination of an event time associated with this detection event signal, determination of an event time skew based on an energy of this detection event signal and the first relationship, determination of a corrected event time based on the event time and the event time skew, and identification of a coincidence based on the corrected event time.

20 Claims, 15 Drawing Sheets

(56) References Cited

OTHER PUBLICATIONS

Shao, Yiping "A new timing model for calculating the intrinsic timing resolution of a scintillator detector", Physics in Medicine and Biology, vol. 52 (2007), DOI:10.1088/0031-9155/52/4/016, (pp. 1103-1117, 15 total pages).
Derenzo, Stephen E. et al., "Fundamental limits of scintillation detector timing precision", Physics in Medicine and Biology, vol. 59, (2014), DOI:10.1088/0031-9155/59/13/3261, (pp. 3261-3286, 27 total pages).

\* cited by examiner

TEMPERATURE-SENSITIVE TRIGGER SKEW CORRECTION

BACKGROUND

According to conventional positron-emission-tomography (PET) imaging, a radiopharmaceutical tracer is introduced into a patient body typically via arterial injection. Radioactive decay of the tracer generates positrons which eventually encounter electrons and are annihilated thereby. Annihilation produces two photons which travel in approximately opposite directions.

A ring of detectors surrounding the body detects the emitted photons, identifies "coincidences", and reconstructs PET images based on the identified coincidences. A coincidence is identified when two detectors disposed on opposite sides of the body detect the arrival of two photons within a particular coincidence time window. Because the two "coincident" photons travel in approximately opposite directions, the locations of the two detectors determine a Line-of-Response (LOR) along which an annihilation event may have occurred.

The foregoing process requires extreme accuracy in the determination of arrival times of photons at the detectors. Arrival of a photon at a detector (e.g., a scintillator combined with silicon photomultipliers (SiPMs), a scintillator combined with photomultiplier tubes (PMTs), semiconductor based detectors) causes the detector to generate an electrical signal. Generally, a photon arrival time is identified as a time (i.e., a "trigger" time) at which the generated electrical signal crosses a threshold voltage. Ideally, the shape and peak magnitude of the electrical signal is identical for all events detected by all detectors in the PET ring, allowing arrival times to be consistently compared in order to identify coincidences.

However, the shape and/or peak magnitude of detector-generated signals may differ across detectors due to detector heterogeneities, due to partial photon energy deposition, and due to temperature differences. The differences in shape and/or peak magnitude may result in differences in the times at which the electrical signals cross the threshold voltage. Consequently, two photons resulting from a single annihilation and received by two oppositely-disposed detectors may be determined as arriving outside of the coincidence time window and therefore not identified as a coincidence. Similarly, two photons resulting from two different annihilations may be determined as arriving within the coincidence time window and therefore identified as a coincidence.

Systems are desired to correct for skew in the trigger time caused by temperature and energy effects. Some systems attempt to correct for partial photon energy deposition effects by applying an individualized scaling factor to each event signal to bring the event signals to a same target peak amplitude, but these systems do not determine any trigger timing skew due to such effects. Known systems also attempt to correct for temperature-based trigger skew. However, these systems use hardware temperature sensors mounted to a detector circuit board to detect temperature and correct event signals based on predetermined temperature-dependent calibration data. Hardware temperature sensors are costly, present a significant latency between temperature sensor response and the actual increase in detector temperature, and also fail to detect actual detector temperature due to their mounting locations.

BRIEF DESCRIPTION OF THE DRAWINGS

FIGS. 12a and 10b comprise a flow diagram of a process to determine a corrected event time according to some embodiments.

DETAILED DESCRIPTION

Figure 1A:
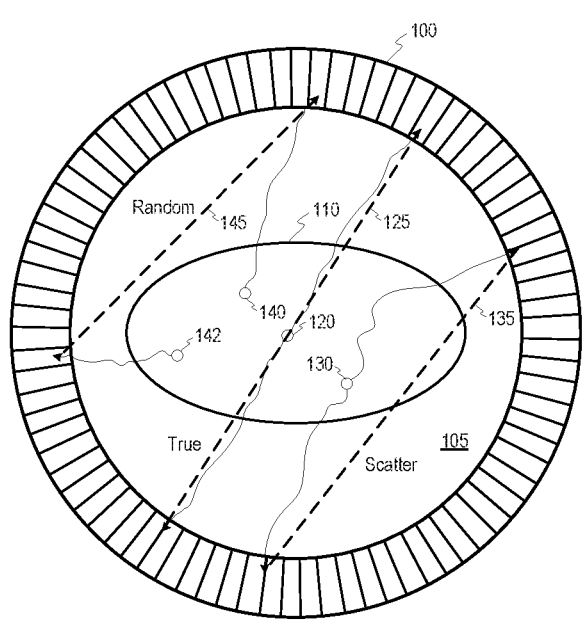
FIGS. 1a and 1b illustrate detection of coincidence events according to some embodiments.

The following description is provided to enable any person in the art to make and use the described embodiments and sets forth the best mode contemplated for carrying out the described embodiments. Various modifications, however, will remain apparent to those in the art.

A semiconductor-based photodetector is temperature-sensitive. Specifically, a photodetector's temperature influences its photoelectron amplification gain, and therefore the trigger times which are determined based on its output signal. Some embodiments mitigate the issues of trigger time skew caused by the temperature and energy deposition variance.

Generally, some embodiments determine a first relationship between change in trigger time (i.e., trigger skew) and change in event energy at a first temperature and a second relationship between change in trigger time and change in event energy based on a photopeak energy at a first temperature and a photopeak energy at a second temperature. These relationships are then used to correct the trigger time determined for event signals.

In particular, a trigger time of an event detection signal is determined based on a trigger threshold according to conventional systems. The energy of the event detection signal is also determined, and a difference between the determined energy and a target energy corresponding to the photopeak is determined. This difference is multiplied by the first relationship and the second relationship to determine a trigger skew. The trigger skew is added to the determined trigger time to obtain a corrected trigger time for the event detection signal. The corrected trigger time may then be compared with similarly-corrected trigger times of other event detection signals to identify coincidences.

The second relationship may be periodically re-determined during scanning to account for temperature changes. For example, if the photopeak energy changes (as it would due to a temperature change), a new second relationship between change in trigger time and change in event energy is determined based on the photopeak energy at the first temperature and the changed photopeak energy. The new second relationship is then used with the first relationship as described above to determine a trigger skew for newly-output event detection signals.

Some embodiments provide dynamic correction of trigger skew, thereby improving timing accuracy and enhancing PET timing resolution. Embodiments may further provide an algorithm capable of real-time execution by a Field-Programmable Gate Array (FPGA) using a lookup table (LUT) to perform the required multiplications. Process latency is also reduced by avoiding a hardware temperature readout feedback loop. Elimination of the need for hardware temperature sensors may reduce product cost and improve design flexibility by allowing future improvements to detector function to be implemented via firmware upgrades rather than hardware upgrades.

Magnetic Resonance (MR)-PET imaging systems acquire MR and PET images via simultaneous MR and PET scans. The MR scan may result in high magnitude and rapid temperature fluctuations within the PET detectors during the PET scan. In particular, execution of MR RF and gradient (e.g., echo planar imaging (EPI)) sequences may result in magnetic field transients which induce currents within the detectors, which in turn heat the detectors. Systems for continuous real-time temperature-responsive trigger skew correction may therefore be particularly beneficial for use in MR-PET imaging systems.

Generally, a PET detector includes one or more scintillation elements and one or more electrical transducers. The scintillation elements create photons with the energy of few electron volts (eV) in response to receiving the 511 keV photons which result from annihilation events. Lutetium oxyorthosilicate (LSO) and other scintillators exhibit suitable stopping power and fast scintillation decay, and may be used in high count rate scenarios. The electrical transducers convert the low-energy photons created by the scintillation elements to electrical signals, referred to herein as detection event signals and event signals. According to some embodiments, the electrical transducers may comprise, for example, SiPMs, PMTs, or semiconductor-based detectors.

The detected events may be stored as raw (i.e., list-mode) data and/or sinograms. List-mode data may represent each annihilation event using data specifying a LOR and the time at which the event occurred. Time-of-flight (TOF) PET additionally measures the difference between the detection times of the two 511 keV photons arising from the annihilation event. This difference may be used to more accurately estimate a particular position along the LOR at which the annihilation event occurred. Both coincidence detection and TOF determinations require accurate and consistent determination of actual arrival times corresponding to detected event.

Figure 1B:
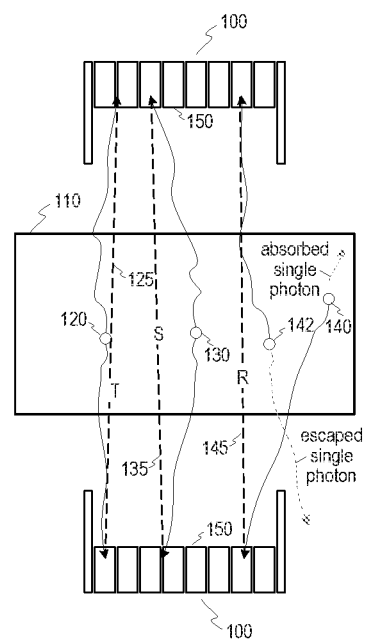

FIG. 1a and FIG. 1b illustrate detection of coincidence events according to some embodiments. FIG. 1a is an axial view of bore 105 of detector ring 100 and imaging subject 110 disposed therein. Imaging subject 110 may comprise a human body, a phantom, or any other suitable subject. FIG. 1b is a transaxial view of detector ring 100 and body 110 of FIG. 2a. Detector ring 100 is composed of an arbitrary number (eight in this example) of adjacent and coaxial rings of detectors 150 in the illustrated example. Each detector 150 may comprise any number of scintillator crystals and electrical transducers.

Annihilation events 120, 130, 140 and 142 are assumed to occur at various locations within subject 110. As described above, an injected tracer generates positrons which are annihilated by electrons to produce two 511 keV photons which travel in approximately opposite directions. Each represented annihilation event results in the detection of a coincidence. True coincidences represent valid image data, while scatter and random coincidences represent noise associated with incorrect event position information.

A coincidence is detected when a pair of detectors receive two annihilation photons within the coincidence time window, as determined based on the calculated arrival times of the two annihilation photons at their respective detectors. Event 120 is associated with a true coincidence because event 120 resulted in two photons which were received within the coincidence time window and because the position of annihilation event 120 lies on LOR 125 connecting the detector positions at which the two photons were received.

Event 130 is associated with a scatter coincidence because, even though the two photons resulting from event 130 were detected within the coincidence time window, the position of annihilation event 130 does not lie on LOR 135 connecting the two photon positions. This may be due to Compton (i.e., inelastic) or Coherent (i.e., elastic) scatter resulting in a change of direction of at least one of the two annihilation photons within subject 110.

Events 140 and 142 are two separate annihilation events which result in detection of a random coincidence. In the present example, one of the photons generated by event 140 is absorbed in body 210 and one of the photons generated by event 142 escapes detection by any detector 150 of detector ring 100. The remaining photons happen to be detected within the coincidence time window, even though no annihilation event occurred on LOR 145 connecting the positions at which the coincident photons were received.

Since only the true unscattered coincidences indicate locations of annihilation events, random coincidences and scatter coincidences are often subtracted from or otherwise used to correct acquired PET data during reconstruction of a PET image.

Figure 2:
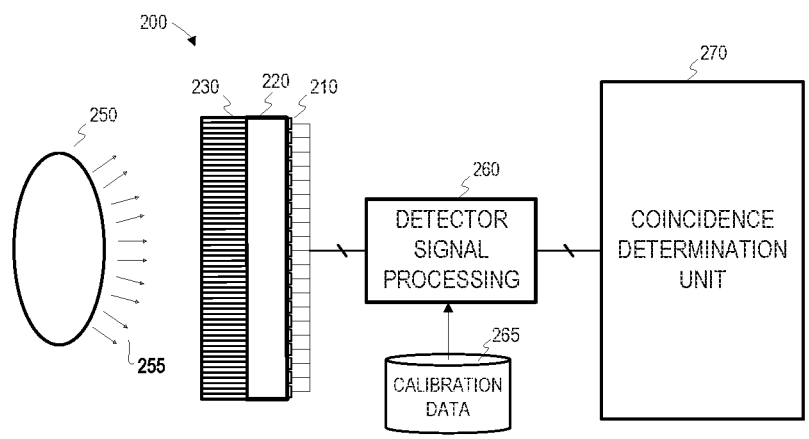
FIG. 2 is a block diagram of a coincidence determination system according to some embodiments.

FIG. 2 illustrates PET detector ring portion 200 according to some embodiments. Detector 200 includes detectors 210, optional light guide 220 and scintillator 230. Scintillator 230 may be pixelated (as shown) or monolithic.

Detector ring portion 200 is positioned to detect gamma rays 255 emitted from volume 250. Systems for facilitating the emission of gamma rays from a volume are known in the art, and in particular with respect to the PET imaging described herein. As described above, scintillator 230 receives the gamma rays 255 and emits photons in response. Detectors 210 receive the photons and each detector 210 generates electrical signals based on the energy of received photons and its own characteristic photoelectric response profile.

Embodiments are not limited to scintillator-based detectors. Direct conversion detectors (e.g., CZT and TIBr) may also be used in conjunction with some embodiments.

Detector signal processing unit 260 receives the electrical signals generated by each detector 210 and performs signal processing to, for example, determine whether a signal represents a photon detection event, perform signal unpiling by pile-up rejection, determine an event energy, and determine an event time. As will be described below, determination of the event time corresponding to a signal output by a detector 210 may utilize predetermined calibration data 265 associated with the detector. Detector signal processing unit 260 may perform any suitable functions and exhibit any suitable implementations.

Coincidence determination unit 270 receives all photon detection events which pass energy qualification, called singles, and their corresponding corrected event times as described herein, and identifies pairs of events which occurred within a coincidence time window.

Figure 3A:
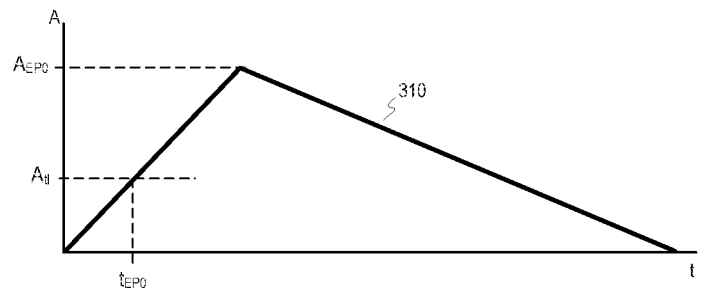
FIG. 3a illustrates a full energy deposition event signal and event timing determination according to some embodiments.

In order to assist the following discussion, FIG. 3a illustrates event signal 310 output by a detector, and which represents a target energy deposition and detector response. As will be described below, signal 310 corresponds to a photopeak within a spectrum of acquired event signals. The shape of event signal 310 is approximated and does not represent a typical detector response, which is a higher-order function.

Trigger level $A_{tl}$ represents a trigger level voltage which defines the event time associated with the event which caused signal 310. Specifically, the event time is defined as the time at which signal 310 crosses trigger level voltage $A_{tl}$, or time $t_{EP0}$. The index EP0 is intended to indicate that event signal 310 exhibits an energy level corresponding to photopeak P0.

Figure 3B:
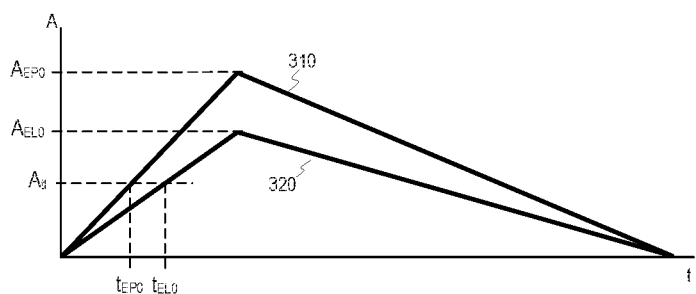
FIG. 3b illustrates a full energy deposition event signal, a partial energy deposition event signal and corresponding different event timing determinations according to some embodiments.

FIG. 3b illustrates signal 310 and partial energy deposition event signal 320. Signal 320 has a peak magnitude $A_{EL0}$, which is lower than peak magnitude $A_{EP0}$ of signal 310. It is assumed that signal 320 is acquired at substantially the same temperature as signal 310, therefore differences therebetween are due to partial energy deposition as is known in the art.

Due to the reduced peak magnitude of signal 320, signal 320 crosses trigger level voltage $A_{tl}$ at time $t_{EL0}$, which is after time $t_{EP0}$. The difference between time $t_{EL0}$ and time $t_{EP0}$ is referred to herein as trigger skew. Absent correction, the photon arrivals which caused signals 310 and 320 may be determined as not falling within a coincidence time window even if in fact they were generated based on a same annihilation event.

Figure 3C:
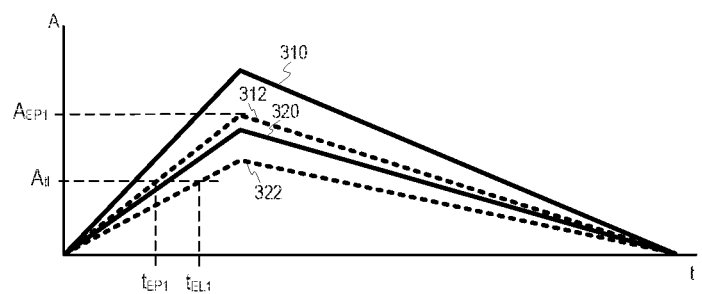
FIG. 3c illustrates a full energy deposition event signal, a full energy deposition event signal acquired at an increased raised temperature, a partial energy deposition event signal, a partial energy deposition event signal acquired at an increased temperature and corresponding different event timing determinations according to some embodiments.
Figure 3D:
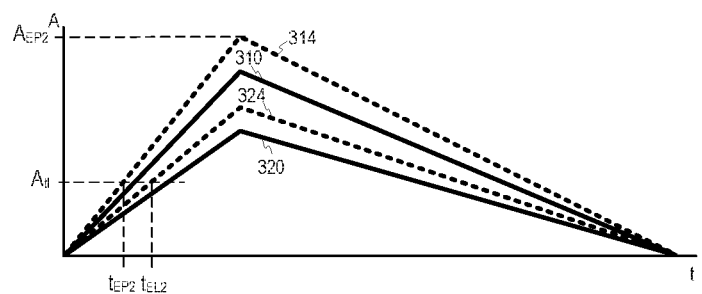
FIG. 3d illustrates a full energy deposition event signal, a full energy deposition event signal acquired at a decreased temperature, a partial energy deposition event signal, a partial energy deposition event signal acquired at a decreased temperature and corresponding different event timing determinations according to some embodiments.

FIGS. 3c and 3d are intended to illustrate the effects of temperature on signals 310 and 320. Increases in temperature may reduce the gain of a SiPM detector, resulting in generation of dashed event signals 312 and 322 of FIG. 3c in response to the same energy photons which resulted in respective event signals 310 and 320 at a lower temperature. As shown, the lower-energy signals result in movement of trigger times $t_{EP0}$ and $t_{EPL}$ forward to trigger times $t_{EP1}$ and $t_{EL1}$, resulting in additional trigger skew.

Similarly, as shown in FIG. 3d, decreases in temperature may increase the gain of a SiPM detector, resulting in generation of dashed event signals 314 and 324 in response to the same energy photons which resulted in respective event signals 310 and 320 at a higher temperature. The higher-energy signals result in movement of trigger times $t_{EP0}$ and $t_{EPL}$ backward to trigger times $t_{EP2}$ and $t_{EL2}$, and corresponding trigger skew.

Figure 4:
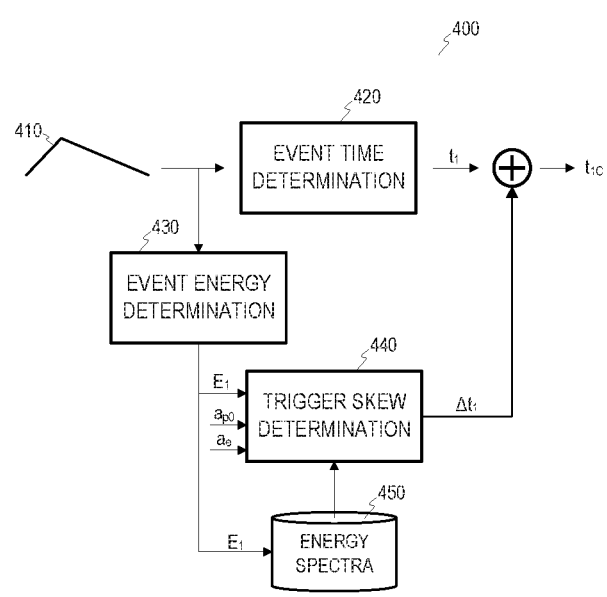
FIG. 4 illustrates a system to correct determined event timing based on partial energy deposition and temperature change according to some embodiments.

FIG. 4 is a block diagram of system 400 to correct trigger skew caused by partial energy deposition and temperature changes. As described above, implementations of system 400 may advantageously perform such correction without use of temperature sensors and in near real-time using simple calculations. Embodiments are not limited to system 400. The components of system 400 may be implemented by any suitable combination of hardware and software.

As illustrated, signal 410 output from a PET detector is received by event time determination unit 420. Unit 420 may determine event time $t_1$ based on a threshold trigger voltage as described above. Event energy determination unit 430 also receives signal 410 and determines an energy value $E_1$ associated with signal 410. Such a determination may comprise integrating signal 410. The energy value $E_1$ is then transmitted to trigger skew determination unit 440.

Trigger skew determination unit 440 determines trigger skew $\Delta t_1$ based on energy value $E_1$ and on parameters $a_e$ and $a_{p0}$. As will be described below, parameter $a_e$ relates trigger skew to changes in event energy at a first temperature and parameter $a_{p0}$ relates trigger skew to changes in event energy based on a photopeak energy at a first temperature and a photopeak energy at a second temperature. Determined trigger skew $\Delta t_1$ is added to event time $t_1$ to generate corrected event time $t_{1c}$. The foregoing process is applied to every detection event signal output by each detector in the PET ring, allowing comparison of the resulting corrected event times to detect coincidences.

Due to the temperature-sensitive gain of the PET detectors, the energy value associated with the photopeak changes as the temperature changes. According to some embodiments, each determined energy value is collected to generate an up-to-date energy spectrum 450. Once enough values (i.e., event counts) have been collected, trigger skew determination unit 440 uses energy spectrum 450 to determine an energy value which corresponds to a current photopeak, which reflects the current temperature. Unit 440 then updates $a_{p0}$ to reflect the new photopeak (i.e., P1) and incoming event signals continue to be processed as described above. System 400 may therefore provide skew correction to address real-time changes in detector gain caused by temperature changes.

Figure 5A:
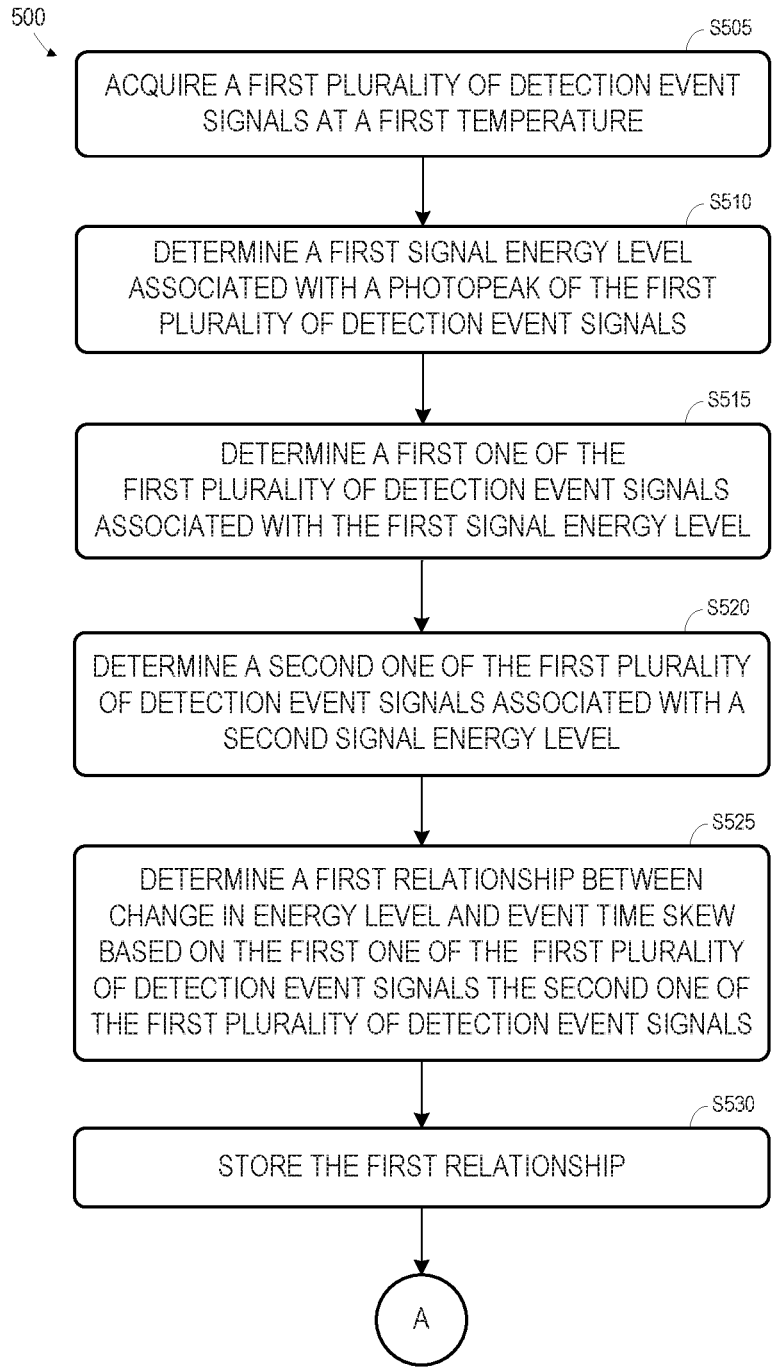
FIGS. 5a and 5b comprise a flow diagram of a process to determine a relationship between signal energy level and event time skew at a given temperature, and a relationship between signal energy level and event time skew given a change in temperature according to some embodiments.
Figure 5B:
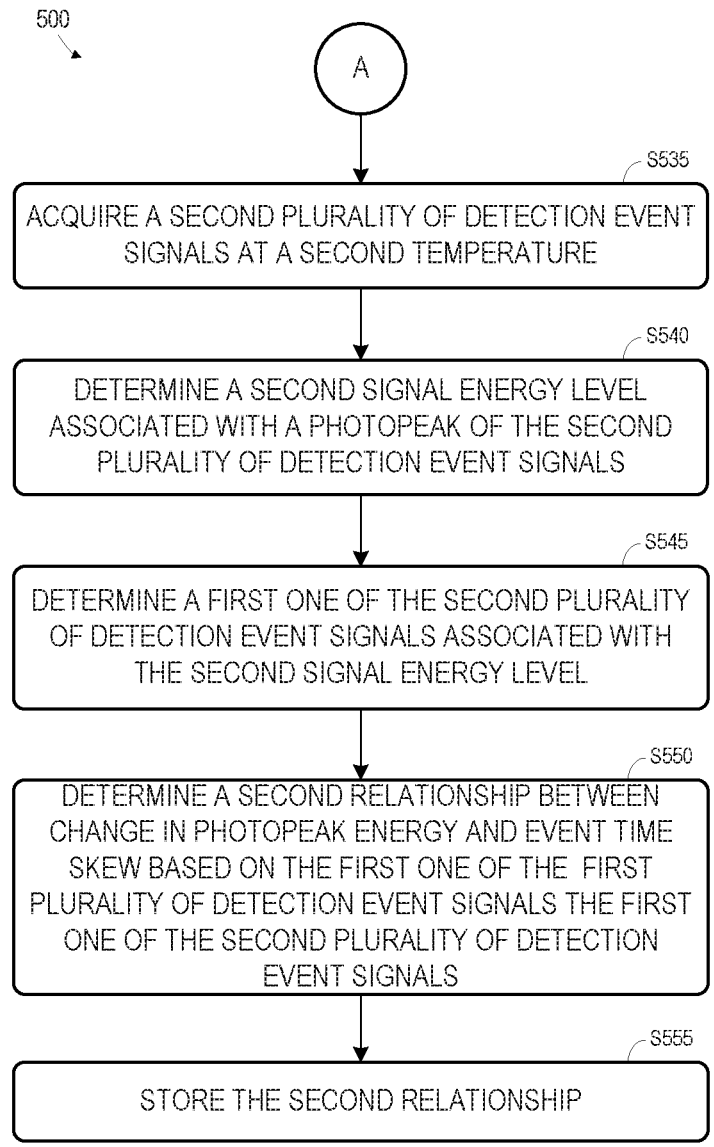

FIGS. 5a and 5b comprise a flow diagram of process 500 to determine a relationship between signal energy level and event time skew at a given temperature, and a relationship between signal energy level and event time skew given a change in temperature according to some embodiments. The determined relationships may be detector-specific, in which case process 500 is executed, in parallel, for each detector (i.e., each entity capturing a gamma-ray and emitting a corresponding detection event signal) in a PET imaging system.

Process 500 may be executed during a calibration mode in order to determine the above-described relationships and store the relationships for use during runtime operation of the detectors, as will be described below with respect to process 1200.

Flow diagram 500 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape, and executed by any suitable processing unit, including but not limited to one or more microprocessors, microcontrollers, processing cores, and processor threads. Embodiments are not limited to the examples described below.

A first plurality of detection event signals are acquired at S505. The detection event signals may be acquired by a conventional static or rotational PET scan after injection of a radionuclide tracer into a volume as is known in the art. The first plurality of detection event signals are acquired while the acquiring detector is at a first temperature. For example, the first temperature may be 25 degrees Celsius.

Figure 6:
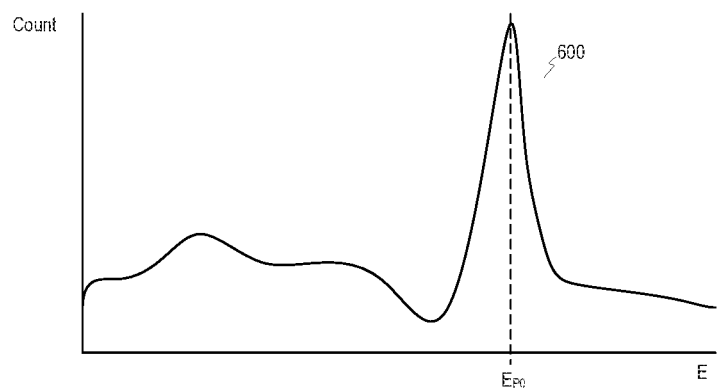
FIG. 6 is a graph of energy versus event counts to illustrate photopeak determination according to some embodiments.

Next, at S510, a first signal energy level is determined. The first signal energy level is an energy level associated with a photopeak of the first plurality of detection event signals. According to some embodiments of S510, the energy level of each of the first plurality of detection event signals is determined and the determined energy levels are binned into an energy spectrum such as energy spectrum 600 of FIG. 6. Due to the predominance of fully-deposited 511 keV gamma-ray photons, energy spectrum 600 exhibits a peak at one particular energy bin, denoted $EP_0$. The actual value of $E_{P0}$ depends on the detector components and the temperature during acquisition.

A first one of the first plurality of signals which is associated with the first signal energy level (i.e., $E_{P0}$) is determined at S515. Then, at S520, a second one of the first plurality of signals which is associated with a second signal energy level is determined. The second signal energy level may be equal to any other energy level represented in the energy spectrum.

Figure 7:
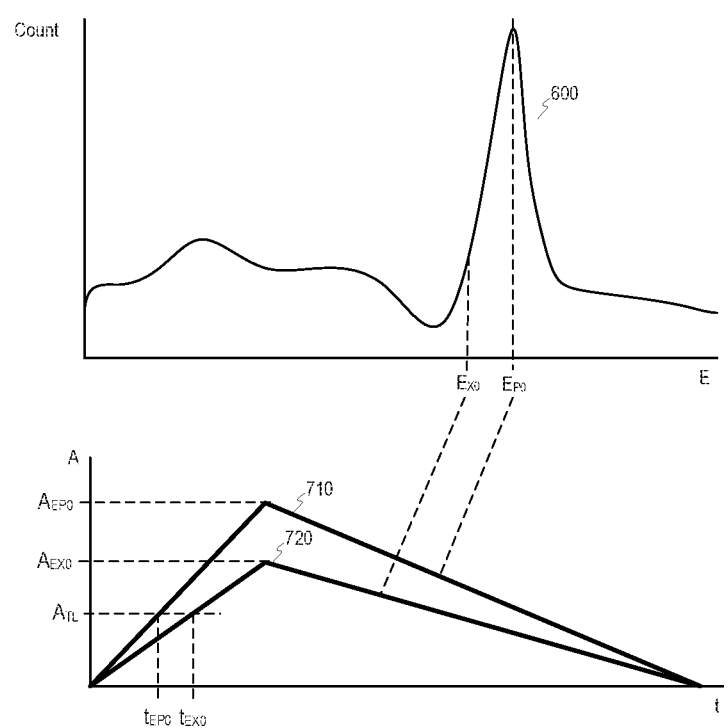
FIG. 7 illustrates a relationship between signal energy level and event time skew at a given temperature according to some embodiments.

FIG. 7 illustrates the determinations at S515 and S520, showing first event signal 710 which exhibits an energy level equal to $E_{P0}$, and second event signal 720 which exhibits an energy level equal to another energy level of spectrum 600, denoted $E_{X0}$. As shown, signal 710 exhibits a peak amplitude $A_{EP0}$ and signal 720 exhibits a peak amplitude $A_{EX0}$. Additionally, based on trigger level $A_{tl}$, first event signal 710 is associated with an event time of $t_{EP0}$ and second event signal 720 is associated with an event time of $t_{EX0}$.

The time skew $\Delta t=(t_{EX0}\ t_{EP0})$ and may be determined from the peak amplitudes $A_{EP0}$ and $A_{EX0}$ as:

$$\Delta t = \frac{A_{EXO} - b_X}{s_X} - \frac{A_{EPO} - b_P}{s_P},$$

where $s_X$ and $s_P$ are the slopes of the initial upward portions of signals 720 and 710 and $b_X$ and $b_P$ are the y-intercepts, respectively.

Figure 8:
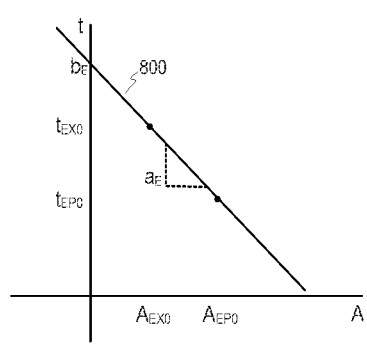
FIG. 8 illustrates a relationship between change in signal energy level and event time skew at a given temperature according to some embodiments.

At S525, a first relationship is determined between change in signal energy level and event time skew. FIG. 8 illustrates a graph of peak amplitude vs. trigger time, showing points $(A_{EP0}, t_{EP0})$ and $(A_{EX0}, t_{EX0})$ taken from FIG. 7. The first relationship determined at S525 therefore consists of slope $a_E$ and y-intercept $b_E$ of line 800 which includes these two points.

The first relationship is stored at S530 so that it may be used to determine trigger times of signals generated by the detector used to acquire the first plurality of detection event signals at S515, as will be described below.

A second plurality of detection event signals are acquired at S535. The second plurality of detection event signals are acquired while the acquiring detector (i.e., the detector which acquired the signals at S515) is at a second temperature. For example, the second temperature may be 27 degrees Celsius.

Figure 9:
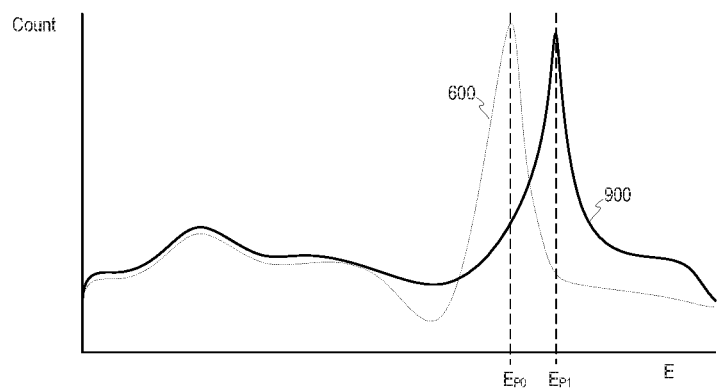
FIG. 9 is a graph of energy versus event counts to illustrate photopeak determination at a second temperature according to some embodiments.

A second signal energy level associated with a photopeak of the second plurality of detection event signals is determined at S540. FIG. 9 shows energy spectrum 900 of the energy levels of the second plurality of detection event signals. For comparison, FIG. 9 also shows prior energy spectrum 600. As shown, the photopeak has moved from $E_{P0}$ to $E_{P1}$ (i.e., the gain of the detector has decreased) due to the increase in temperature.

Figure 10:
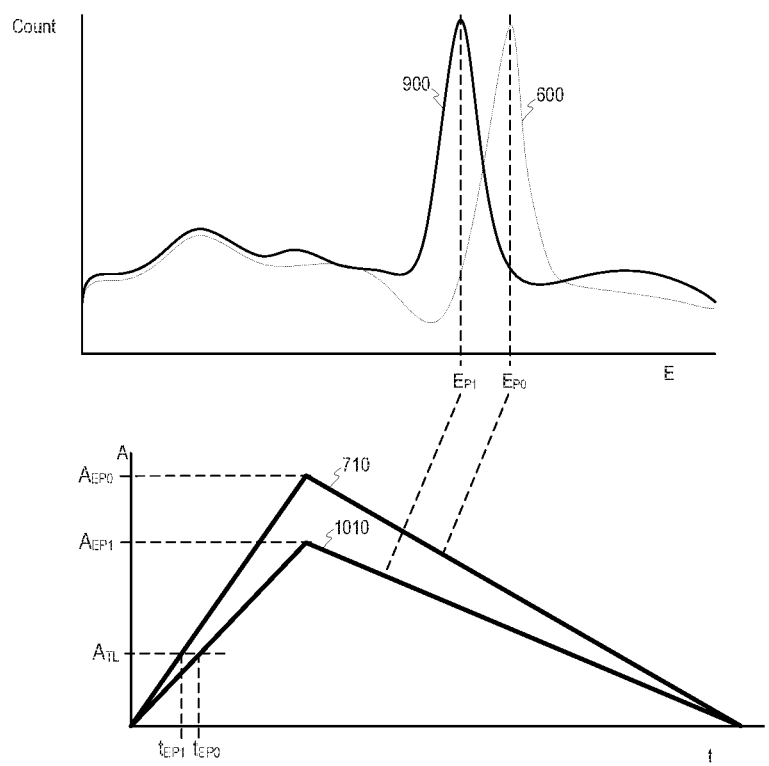
FIG. 10 illustrates a relationship between signal energy level and event time skew given a change in temperature according to some embodiments.

A first one of the first plurality of signals which is associated with the second signal energy level (i.e., Epi) is determined at S545. FIG. 10 illustrates the determination at S545, showing signal 1010 which exhibits an energy level equal to $E_{P1}$. Also shown is event signal 710 determined at S515, which exhibits an energy level equal to $E_{P0}$. Signal 710 exhibits a peak amplitude $A_{EP0}$ and signal 1010 exhibits a peak amplitude $A_{EX0}$. Based on trigger level $A_{tl}$, event signal 710 remains associated with an event time of $t_{EP0}$ and signal 1010 is associated with an event time of $t_{EP1}$.

Figure 11:
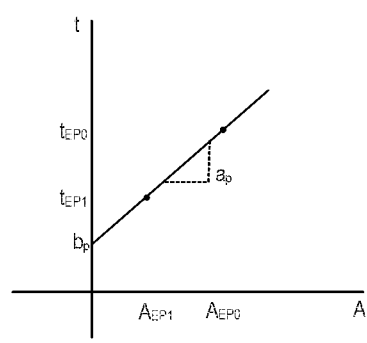
FIG. 11 illustrates a relationship between change in photopeak energy level and event time skew according to some embodiments.

Next, at S550, a second relationship is determined between change in photopeak energy and trigger skew based on the signal determined at S545 (i.e., corresponding to photopeak P1) and the signal determined at S515 (i.e., corresponding to photopeak P0). FIG. 11 illustrates a graph of peak amplitude vs. trigger time for determining the second relationship. Line 1100 of FIG. 11 includes points $(A_{EP0}, t_{EP0})$ and $(A_{EP1}, t_{EP1})$ taken from FIG. 10. The first relationship determined at S550 therefore consists of slope $a_P$ and y-intercept $b_P$ of line 1100 which includes these two points.

The above-described determinations at S525 and S550 use peak amplitude (e.g., $A_{P0}$ and $A_{X0}$) as a proxy for signal energy level, but these determinations may use energy levels (e.g., $E_{P0}$ and $E_{X0}$) instead of peak amplitudes according to some embodiments.

The second relationship is stored at S555 so that it may be used to determine trigger times of signals generated by the current detector. According to some embodiments, a ring of PET detectors includes hardware memory to store calibration data and the first relationship (e.g., $a_E$, $b_E$) and the second relationship (e.g., $a_P$, $b_P$) are stored for each detector of the ring.

Figure 12A:
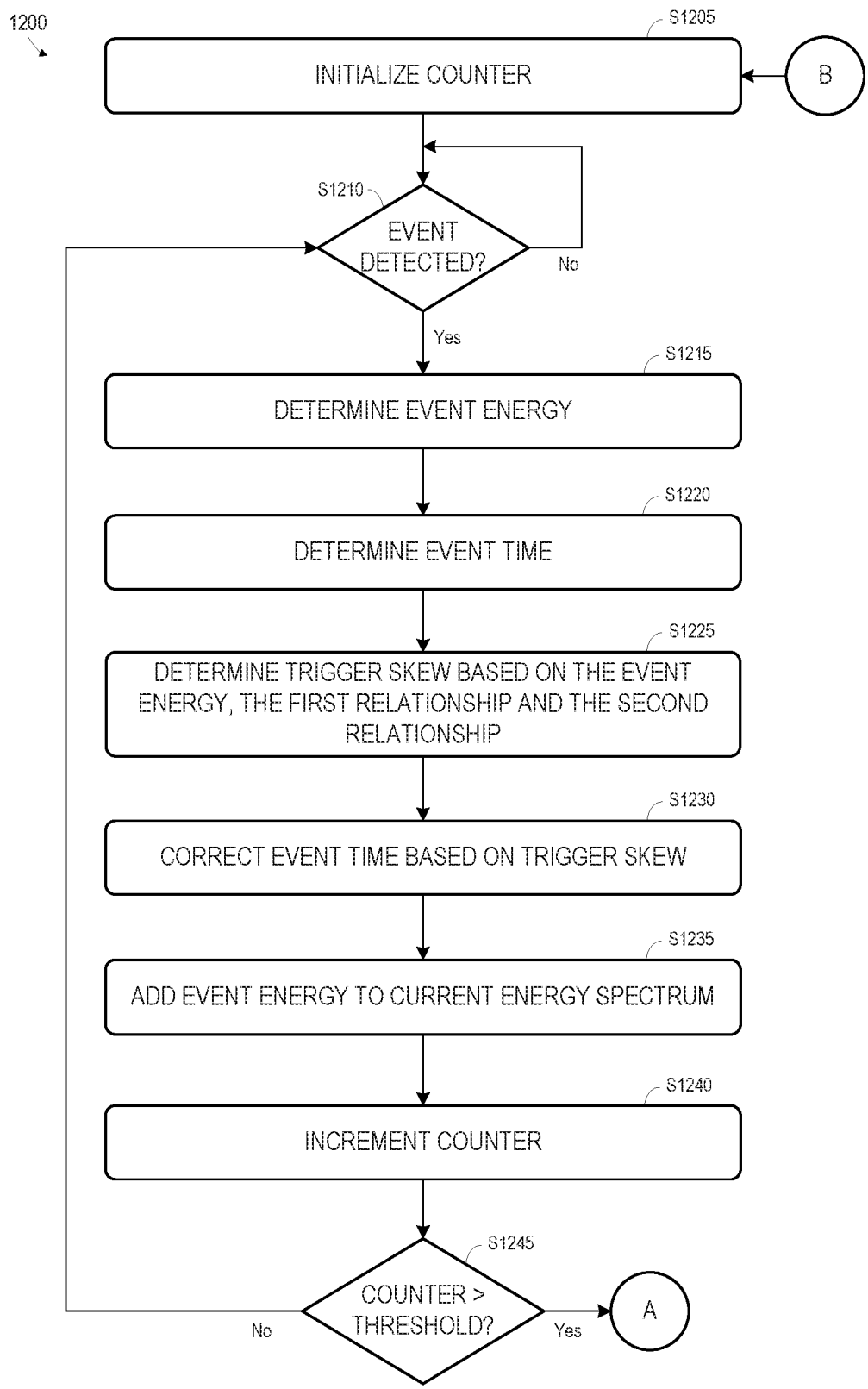
Figure 12B:
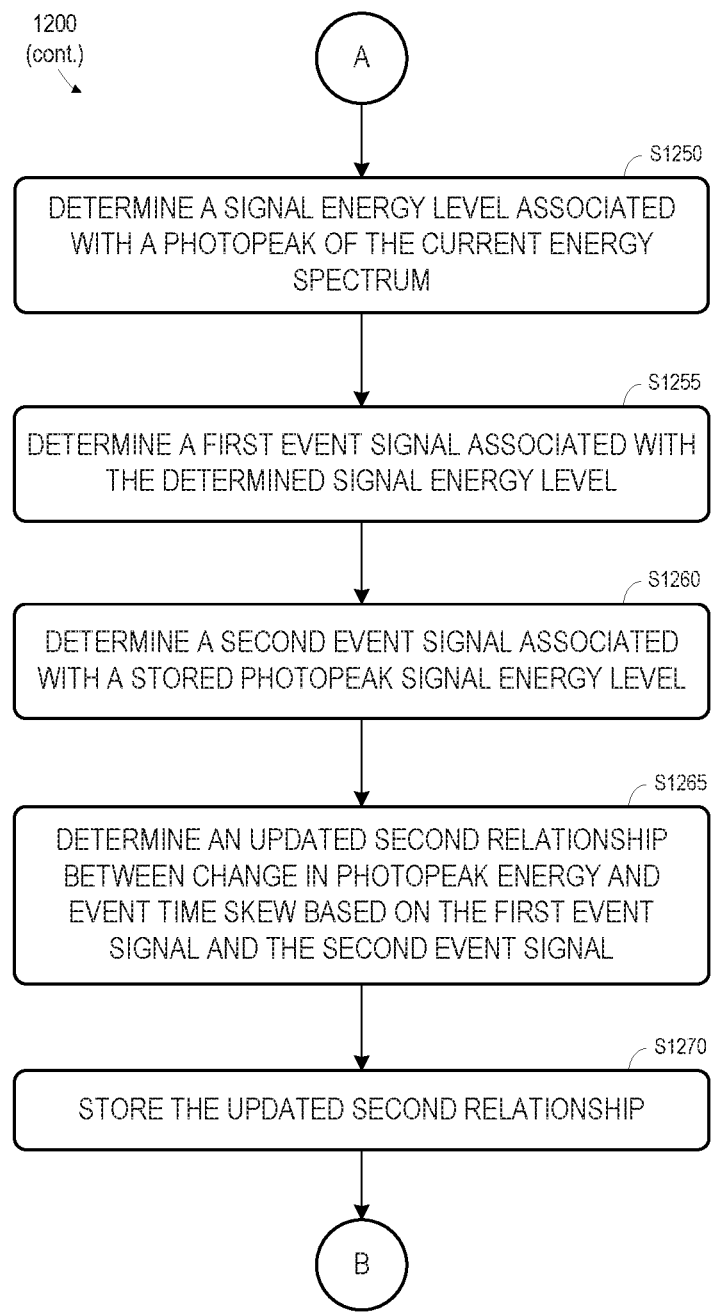

FIGS. 12a and 12b comprise a flow diagram of process 1200 according to some embodiments. Process 1200 is executed during a PET scan to correct trigger skew caused by partial energy deposition and temperature change. Process 1200 is applicable to event signals output by a single detector. It should be noted that process 1200 may be performed, in parallel, for every detector of a PET detector ring during a PET scan.

As described above, process 1200 may be performed without use of a hardware temperature sensor, and may be performed in near real-time. The PET scan may occur simultaneously with other scans, such as an MR scan which subjects the PET detectors to rapid temperature changes.

Initially, a counter is initialized at S1205. As will be described below, the counter is used to collect a number of detection event signals suitable to generate an energy spectrum from which a new photopeak may be determined.

Flow cycles at S1210 until the detector detects an event and generates a corresponding event signal. The event may occur after injection of a radionuclide tracer into a volume adjacent to the detector. An energy of the event is determined at S1215 as is known in the art. Next, at S1220, an event time is determined.

Figure 13:
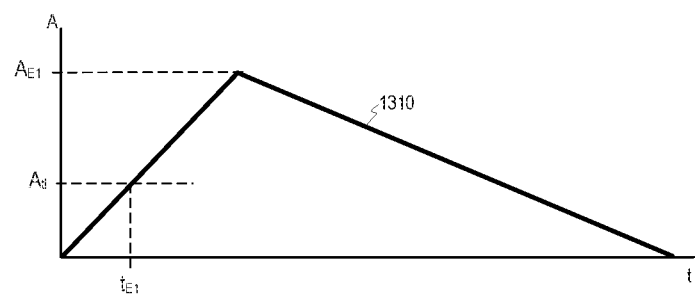
FIG. 13 illustrates an acquired detection event signal and event timing determination according to some embodiments.

FIG. 13 illustrates event signal 1310 which may be generated at S1210. Determination of the event time at S1220 may include determining that signal 1310 crosses threshold voltage level $A_{tl}$ a time $t_{E1}$.

A trigger skew is determined at S1225 based on the determined event energy (E), the energy associated with a known photopeak (e.g., $E_{P0}$), the stored first relationship ($a_E$, $b_E$) determined for the detector, and the stored second relationship ($a_P$, $b_P$) determined for the detector. According to some embodiments, the trigger skew $\Delta t$ is determined at S1225 as:

$$\Delta t = a_P \cdot (a_E \cdot \Delta E) + (b_E + b_P),$$

where $\Delta E = (E - E_{P0})$. In this regard, the energy associated with a known photopeak (e.g., $E_{P0}$) may also be stored in association with the detector during calibration process 500.

Figure 14:
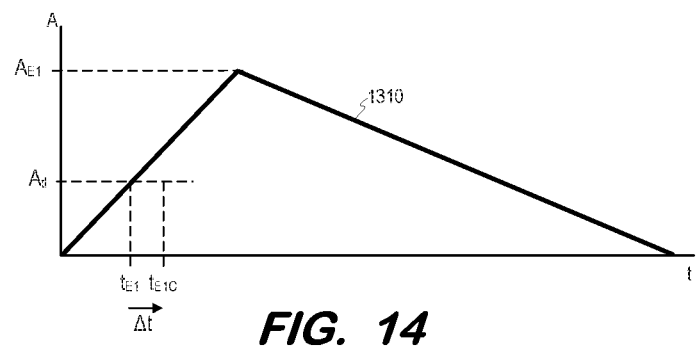
FIG. 14 illustrates correction of the event timing determined in FIG. 13 according to some embodiments.

The determined event time is corrected at S1230 based on the determined trigger skew. According to some embodiments, the trigger skew, which may be a negative or a positive number, is added to the determined event time at S1230. FIG. 14 illustrates correction of determined event time $t_{E1}$ by adding trigger skew $\Delta t$ thereto, resulting in corrected trigger time $t_{E1C}$. This corrected event time may then be compared against other corrected event times corresponding to different events detected by different detectors in order to identify coincidences.

The determined event energy is added to a current energy spectrum at S1235 and the counter is incremented at S1240. It is then determined at S1245 whether the counter is greater than a threshold count. The threshold count is determined so as to reflect a number of counts sufficient to identify a change in the photopeak resulting from a change in temperature. Flow returns to S1210 and continues as described above to determine and correct trigger times of incoming events until it is determined at S1245 that the counter is greater than the threshold.

Flow continues from S1245 to S1250 once it is determined that the counter is greater than the threshold. at S1250, the current spectrum is analyzed to determine a signal energy level corresponding to a photopeak of the current spectrum, as described above. Next, at S1255, a first event signal associated with that energy level is determined, as also described above.

A second event signal associated with a stored photopeak signal energy level is determined at S1260. For example, signal 710 (or, for example, peak amplitude $A_{P0}$ thereof) associated with photopeak P0 may be stored during calibration process 500 and determined at S1260. An updated second relationship ($a_P$, $b_P$) is then determined at S1265 based on the signals determined at S1255 and S1265. The updated second relationship ($a_P$, $b_P$) may be determined as described above with respect to S550 and FIGS. 10 and 11.

The updated second relationship is stored at S1270 and flow returns to S1205 to initialize the counter. Accordingly, events are again detected and their trigger times determined and corrected trigger as described above, but the determination of trigger skew at S1225 now utilizes the updated second relationship. As mentioned above, the updated second relationship may account for any changes in temperature with respect to the calibration temperature used to determine $E_{P0}$. Process 1200 executes continuously during the PET scan in order to correct event times while also regularly updating the second relationship to account for changes in temperature.

Figure 15:
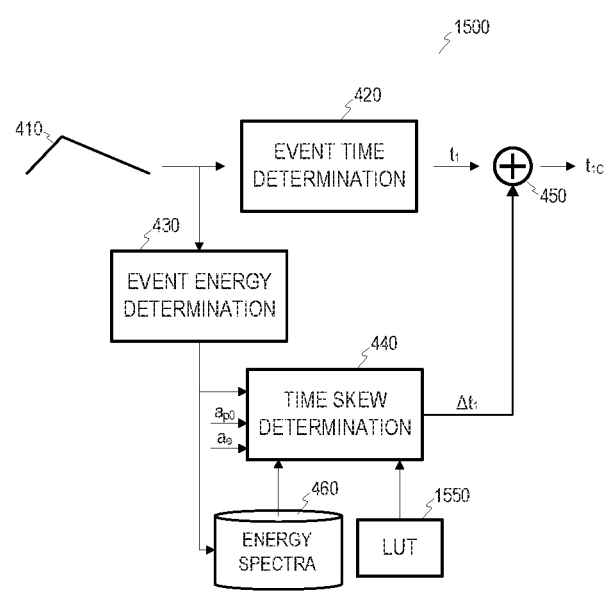
FIG. 15 is a block diagram of a coincidence determination system utilizing a lookup table for calculations according to some embodiments.

FIG. 15 illustrates system 1500 according to some embodiments. System 1500 is identical to system 400 except for lookup table 1550. Lookup table 1550 may store multiplication tables to assist the calculation of $\Delta t$ as described above. The use of lookup table 1550 may allow an FPGA to perform process 1200 to correct trigger times in near real-time. Process 1200 may alternatively be performed by a System-on-a-Chip (SoC) including one or more "real-time" processors. Such implementations may reduce a need for lookup table 1550.

Figure 16:
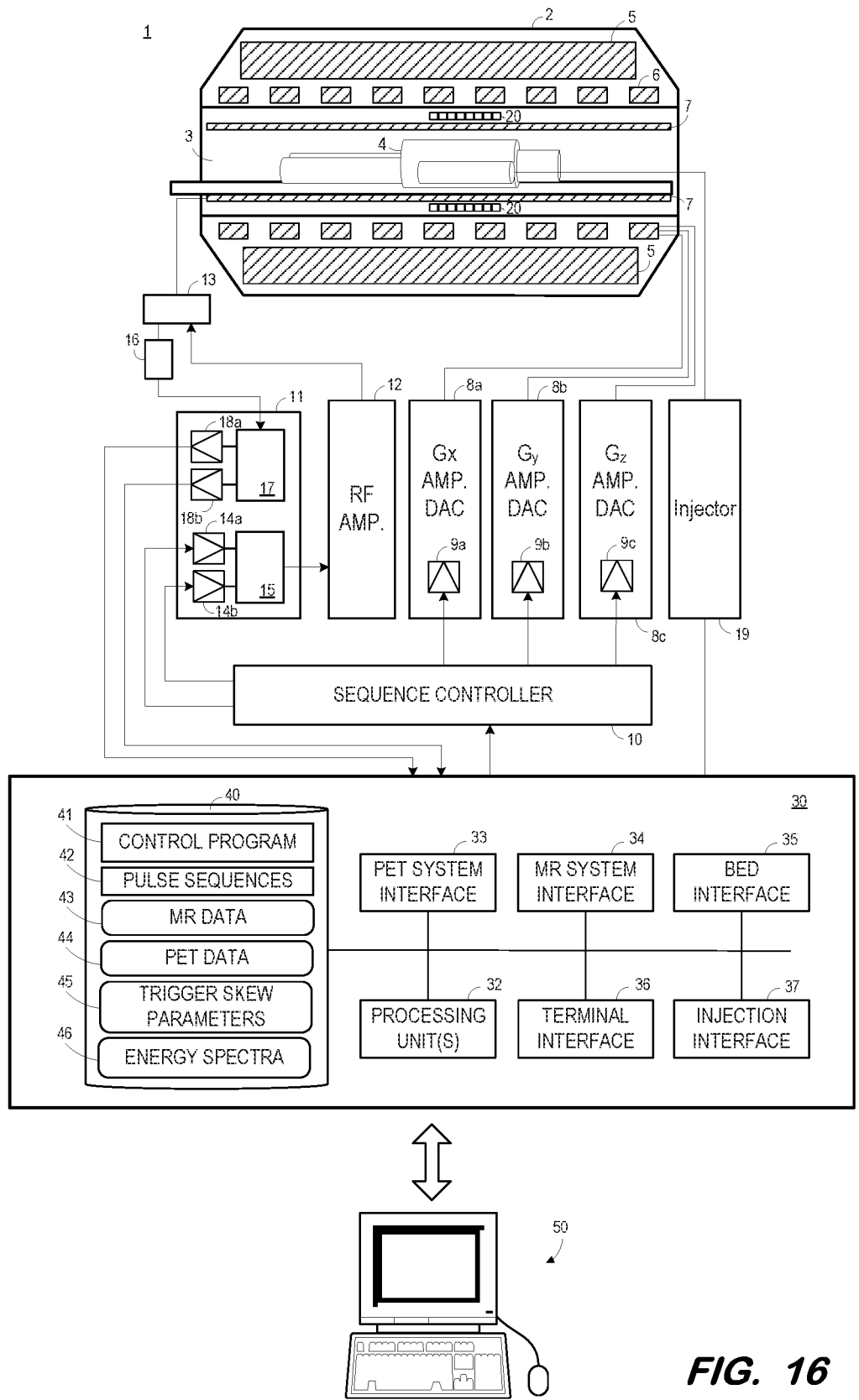
FIG. 16 is a block diagram of an MR-PET imaging system according to some embodiments.

FIG. 16 illustrates MR-PET system 1 for executing MR and PET scans according to some embodiments. System 1 includes MR chassis 2, which defines bore 3 in which patient 4 is disposed. MR chassis 2 includes polarizing main magnet 5, gradient coils 6 and RF coil 7 arranged about bore 3. According to some embodiments, polarizing main magnet 5 generates a uniform main magnetic field ($B_0$) and RF coil 7 emits an excitation field ($B_1$).

Gradient coils 6 produce magnetic field gradients $G_x$, $G_y$, and $G_z$ and are supplied with current by amplifiers 8a-8c. Each amplifier 8a-8c includes a digital-analog converter 9a-9c which is controlled by a sequence controller 10 to generate desired gradient pulses at proper times. Sequence controller 10 also controls the generation of RF pulses by RF system 11 and RF power amplifier 12 using digital-analog converters 14a-14b.

Transmission channel 15 modulates the pulse sequences with a radio-frequency carrier signal having a base frequency corresponding to the resonance frequency of the nuclear spins in the volume to be imaged. The received signals are received by multiplexer 13, amplified by RF amplifier 16 and demodulated in receiving channel 17 of RF system 11 in a phase-sensitive manner. Analog-digital converters 18a and 18b convert the demodulated signals into real and imaginary components from which computing system 30 reconstructs an image according to known techniques.

PET detectors 20 comprise a ring of PET detectors disposed between gradient coils 6 and RF coil 7, but embodiments are not limited thereto. In the illustrated embodiment, the ring is eight PET detectors in width. Each of PET detectors may be calibrated as described with respect to process 500, and trigger times of events detected by each of detectors 20 may be corrected as described with respect to process 1200. The detection and correction may occur during a PET scan performed contemporaneously with an MR scan, which may result in rapid and/or drastic temperature changes within PET detectors 20.

System 30 may comprise any general-purpose or dedicated computing system. Accordingly, system 30 includes one or more processing units 32 (e.g., processors, processor cores, execution threads, etc.) configured to execute processor-executable program code to cause system 30 to operate as described herein, and storage device 40 for storing the program code. Storage device 40 may comprise one or more fixed disks, solid-state random-access memory, and/or removable media (e.g., a thumb drive) mounted in a corresponding interface (e.g., a USB port).

Storage device 40 stores program code of control program 41. One or more processing units 32 may execute control program 41 to provide instructions to sequence controller 10 via MR system interface 34. For example, sequence controller 10 may be instructed to initiate a desired pulse sequence of pulse sequences 42. Sequence controller 10 may be instructed to control the switching of magnetic field gradients via amplifiers 8a-8c at appropriate times, the transmission of radio-frequency pulses having a specified phase and amplitude at specified times via RF system 11 and RF amplifier 12, and the readout of the resulting MR signals to generate MR data 43.

One or more processing units 32 may execute control program 41 to, in conjunction with PET system interface 33, bed interface 35, and injection interface 37, control hardware elements to inject a radioisotope into a patient, move the patient past PET detectors 20, and detect annihilation events occurring within the patient. The detected events may be stored in memory 40 as PET data 44, which may comprise list-mode data and/or sinograms. Detection of the events during scanning may comprise determination of trigger skew based on detector-specific trigger skew parameters 45 and on accumulated energy spectra 46 as described above.

Acquired PET, MR and combined images may be provided to terminal 50 via terminal interface 36 of system 30. Terminal interface 36 may also receive input from terminal 50, which may be used to provide commands to control program 41 in order to control sequence controller 10 and/or other elements of system 1. The commands may include commands to initiate an imaging sequence to acquire image data of a subject. Terminal 50 may simply comprise a display device and an input device coupled to system 30. In some embodiments, terminal 50 is a separate computing device such as, but not limited to, a desktop computer, a laptop computer, a tablet computer, and a smartphone.

Each component of system 1 and other systems described herein may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
   a positron emission tomography scanner comprising a plurality of detectors; and
   a processing unit to:
   determine a first relationship between change in photopeak energy and event time skew based on a first event time of a first detection event signal corresponding to a first photopeak energy level and acquired from a detector at a first temperature and a second event time of a second detection event signal corresponding to a second photopeak energy level and acquired from the detector at a second temperature;
   acquire a third detection event signal from the detector;
   determine an event time associated with the third detection event signal;
   determine an event time skew based on an energy of the third detection event signal and the first relationship;
   determine a corrected event time associated with the third detection event signal based on the event time and the event time skew; and
   identify a coincidence corresponding to the third detection event signal based on the corrected event time.

2. A system according to claim 1, wherein determination of the first relationship comprises:
   acquisition of a first plurality of detection event signals from the detector at the first temperature;
   determination of the first photopeak energy level associated with a photopeak of the first plurality of detection event signals;
   determination of the first detection event signal from the first plurality of detection event signals as associated with the first photopeak energy level;
   acquisition of a second plurality of detection event signals from the detector at the second temperature;
   determination of the second photopeak energy level associated with a photopeak of the second plurality of detection event signals; and
   determination of the second detection event signal from the second plurality of detection event signals as associated with the second photopeak energy level.

3. A system according to claim 1, the processing unit to:
   determine a second relationship between change in photopeak energy and event time skew based on a fourth detection event signal acquired from a second detector at the first temperature and a fifth detection event signal acquired from the second detector at the second temperature;
   acquire a sixth detection event signal from the second detector;
   determine a second event time associated with the sixth detection event signal;
   determine a second event time skew based on an energy of the sixth detection event signal and the second relationship; and
   determine a second corrected event time associated with the sixth detection event signal based on the second event time and the second event time skew,
   wherein the coincidence is identified corresponding to the third detection event signal and the sixth detection event signal based on the corrected event time and the second corrected event time.

4. A system according to claim 1, the processing unit to:
   determine a second relationship between change in energy level and event time skew based on the first detection event signal acquired from a detector at a first temperature and a fourth detection event signal acquired from the detector at the first temperature,
   wherein determination of the event time skew is based on an energy of the third detection event signal, an energy of the first detection event signal, the first relationship and the second relationship.

5. A system according to claim 4, wherein determination of the first relationship comprises:
   acquisition of a first plurality of detection event signals from the detector at the first temperature;
   determination of the first photopeak energy level associated with a photopeak of the first plurality of detection event signals;
   determination of the first detection event signal from the first plurality of detection event signals as associated with the first photopeak energy level;

acquisition of a second plurality of detection event signals from the detector at the second temperature;

determination of the second photopeak energy level associated with a photopeak of the second plurality of detection event signals; and determination of the second detection event signal from the second plurality of detection event signals as associated with the second photopeak energy level.

6. A system according to claim 3, wherein determination of the first relationship comprises:

acquisition of a first plurality of detection event signals from the detector at the first temperature;

determination of the first photopeak energy level associated with a photopeak of the first plurality of detection event signals;

determination of the first detection event signal from the first plurality of detection event signals as associated with the first photopeak energy level;

acquisition of a second plurality of detection event signals from the detector at the second temperature;

determination of the second photopeak energy level associated with a photopeak of the second plurality of detection event signals; and determination of the second detection event signal from the second plurality of detection event signals as associated with the second photopeak energy level, and wherein determination of the second relationship comprises:

acquisition of a third plurality of detection event signals from the second detector at the first temperature;

determination of a third photopeak energy level associated with a photopeak of the third plurality of detection event signals;

determination of the fourth detection event signal from the third plurality of detection event signals as associated with the third photopeak energy level;

acquisition of a fourth plurality of detection event signals from the second detector at the second temperature;

determination of a fourth photopeak energy level associated with a photopeak of the fourth plurality of detection event signals; and determination of the fifth detection event signal from the fourth plurality of detection event signals as associated with the fourth photopeak energy level.

7. A system according to claim 5, wherein determination of the second relationship comprises:

determination of the fourth detection event signal from the first plurality of detection event signals as associated with an energy level different from the first photopeak energy level.

8. A system according to claim 1, the processing unit to:

update the first relationship between change in photopeak energy and event time skew based on an energy spectrum of detection event signals including the third detection event signal;

acquire a fourth detection event signal from the detector;

determine a second event time associated with the fourth detection event signal;

determine a second event time skew based on an energy of the fourth detection event signal and the updated first relationship;

determine a second corrected event time associated with the fourth detection event signal based on the second event time and the second event time skew; and identify a second coincidence corresponding to the fourth detection event signal based on the second corrected event time.

9. A method comprising:

determining a first relationship between change in photopeak energy and event time skew based on a first event time of a first detection event signal corresponding to a first photopeak energy level and acquired from a detector at a first temperature and second event time of a second detection event signal acquired from the detector at a second temperature;

acquiring a third detection event signal from the detector;

determining an event time associated with the third detection event signal;

determining an event time skew based on an energy of the third detection event signal and the first relationship;

determining a corrected event time associated with the third detection event signal based on the event time and the event time skew; and identifying a coincidence corresponding to the third detection event signal based on the corrected event time.

10. A method according to claim 9, wherein determining the first relationship comprises:

acquiring a first plurality of detection event signals from the detector at the first temperature;

determining the first photopeak energy level associated with a photopeak of the first plurality of detection event signals;

determining the first detection event signal from the first plurality of detection event signals as associated with the first photopeak energy level;

acquiring a second plurality of detection event signals from the detector at the second temperature;

determining the second photopeak energy level associated with a photopeak of the second plurality of detection event signals; and determining the second detection event signal from the second plurality of detection event signals as associated with the second photopeak energy level.

11. A method according to claim 9, further comprising:

determining a second relationship between change in photopeak energy and event time skew based on a fourth detection event signal acquired from a second detector at the first temperature and a fifth detection event signal acquired from the second detector at the second temperature;

acquiring a sixth detection event signal from the second detector;

determining a second event time associated with the sixth detection event signal;

determining a second event time skew based on an energy of the sixth detection event signal and the second relationship; and determining a second corrected event time associated with the sixth detection event signal based on the second event time and the second event time skew, wherein the coincidence is identified corresponding to the third detection event signal and the sixth detection event signal based on the corrected event time and the second corrected event time.

12. A method according to claim 9, further comprising:

determining a second relationship between change in energy level and event time skew based on the first detection event signal acquired from a detector at a first temperature and a fourth detection event signal acquired from the detector at the first temperature, wherein determining the event time skew is based on an energy of the third detection event signal, an energy of the first detection event signal, the first relationship and the second relationship.

13. A method according to claim 9, further comprising:
updating the first relationship between change in photopeak energy and event time skew based on an energy spectrum of detection event signals including the third detection event signal;
acquiring a fourth detection event signal from the detector;
determining a second event time associated with the fourth detection event signal;
determining a second event time skew based on an energy of the fourth detection event signal and the updated first relationship;
determining a second corrected event time associated with the fourth detection event signal based on the second event time and the second event time skew; and
identifying a second coincidence corresponding to the fourth detection event signal based on the second corrected event time.

14. A method according to claim 11, wherein determining the first relationship comprises:
acquiring a first plurality of detection event signals from the detector at the first temperature;
determining the first photopeak energy level associated with a photopeak of the first plurality of detection event signals;
determining the first detection event signal from the first plurality of detection event signals as associated with the first photopeak energy level;
acquiring a second plurality of detection event signals from the detector at the second temperature;
determining the second photopeak energy level associated with a photopeak of the second plurality of detection event signals; and
determining the second detection event signal from the second plurality of detection event signals as associated with the second photopeak energy level, and
wherein determining the second relationship comprises:
acquiring a third plurality of detection event signals from the second detector at the first temperature;
determining a third photopeak energy level associated with a photopeak of the third plurality of detection event signals;
determining the fourth detection event signal from the third plurality of detection event signals as associated with the third photopeak energy level;
acquiring a fourth plurality of detection event signals from the second detector at the second temperature;
determining a fourth photopeak energy level associated with a photopeak of the fourth plurality of detection event signals; and
determining the fifth detection event signal from the fourth plurality of detection event signals as associated with the fourth photopeak energy level.

15. A method according to claim 12, wherein determining the first relationship comprises:
acquiring a first plurality of detection event signals from the detector at the first temperature;
determining the first photopeak energy level associated with a photopeak of the first plurality of detection event signals;
determining the first detection event signal from the first plurality of detection event signals as associated with the first photopeak energy level;
acquiring a second plurality of detection event signals from the detector at the second temperature;
determining the second photopeak energy level associated with a photopeak of the second plurality of detection event signals; and
determining the second detection event signal from the second plurality of detection event signals as associated with the second photopeak energy level.

16. A method according to claim 15, wherein determining the second relationship comprises:
determining the fourth detection event signal from the first plurality of detection event signals as associated with an energy level different from the first photopeak energy level.

17. A method comprising: acquiring a first plurality of detection event signals from a detector at a first temperature;
determining a first photopeak energy level associated with a photopeak of the first plurality of detection event signals;
determining a first detection event signal from the first plurality of detection event signals as associated with the first energy photopeak level;
acquiring a second plurality of detection event signals from the detector at a second temperature;
determining a second photopeak energy level associated with a photopeak of the second plurality of detection event signals;
determining a second detection event signal from the second plurality of detection event signals as associated with the second photopeak energy level;
determining a first relationship between change in photopeak energy and event time skew based on a first event time of the first detection event signal and a second event time of the second detection event signal; and
storing the first relationship in association with the detector;
acquiring a third detection event signal from the detector;
determining an event time associated with the third detection event signal;
determining an event time skew based on an energy of the third detection event signal and the first relationship;
determine a corrected event time associated with the third detection event signal based on the event time and the event time skew; and
identify a coincidence corresponding to the third detection event signal based on the corrected event time.

18. A method according to claim 17, further comprising:
determining a fourth detection event signal from the first plurality of detection event signals as associated with an energy level different from the first energy level; and
determining a second relationship between change in energy level and event time skew based on the first detection event signal and the fourth detection event signal.

19. A method according to claim 17, further comprising:
acquiring a third plurality of detection event signals from a second detector at the first temperature;
determining a third photopeak energy level associated with a photopeak of the third plurality of detection event signals;
determining a third detection event signal from the third plurality of detection event signals as associated with the third photopeak energy level;
acquiring a fourth plurality of detection event signals from the second detector at the second temperature;

determining a fourth photopeak energy level associated with a photopeak of the fourth plurality of detection event signals;

determining a fourth detection event signal from the fourth plurality of detection event signals as associated with the fourth photopeak energy level;

determining a second relationship between change in photopeak energy and event time skew based on the third detection event signal and the fourth detection event signal; and storing the second relationship in association with the second detector.

20. A method according to claim 18, further comprising:

acquiring a third detection event signal from the detector;

determining an event time associated with the third detection event signal;

determining an event time skew based on an energy of the third detection event signal, an energy of the first detection event signal, the first relationship and the second relationship;

determining a corrected event time associated with the third detection event signal based on the event time and the event time skew; and identifying a coincidence corresponding to the third detection event signal based on the corrected event time.

* * * * *